United States Patent [19]

Baggiolini et al.

[11] Patent Number: 4,612,308

[45] Date of Patent: Sep. 16, 1986

[54] 25,26-DEHYDRO-1α,23(S,R)-DIHYDROXY-CHOLECALCIFEROL AND ITS EPIMERS

[75] Inventors: Enrico G. Baggiolini, North Caldwell; Gary A. Truitt, Passaic; Milan R. Uskokovic, Upper Montclair; Peter M. Wovkulich, Nutley, all of N.J.

[73] Assignee: Hoffmann-La Roche Inc., Nutley, N.J.

[21] Appl. No.: 676,155

[22] Filed: Nov. 29, 1984

[51] Int. Cl.$^4$ ............................................. A61K 31/59
[52] U.S. Cl. ................................. 514/167; 260/397.2; 568/379; 568/664
[58] Field of Search ...................... 260/397.2; 514/167

[56] References Cited

U.S. PATENT DOCUMENTS 4,391,802  7/1983  Suda et al. ......................... 514/167

OTHER PUBLICATIONS

Dokoh, S. et al., The Ovary: A Target Organ for 1,25-dihydroxyvitamin $D_3$, *Endocrinology* 112: 200–206, 1983.
Murao, S., Control of Macrophage Cell Differentiation in Human Promyelocytic HL-60 Leukemia Cells by 1,25-dihydroxyvitamin $D_3$ and phorbol-12-myristate-13-acetate, *Cancer Res.* 43 (8): 4989–4996, 1983.
Reitsma, P. et al., Vitamin $D_3$ Regulates c-myc Oncogene Expression in HL-60 Leukemic Cells, *J. Cell Biol.* 97 (5): 347a, 1983.
Rigby, W. F. C. et al., 1,25-Dihydroxyvitamin $D_3$ Induces Granulocytic Differention and Myeloid Specific Antigens in the HL-60 Promyelocytic Leukemia Cell Line, *Blood* 62 (5): 153a, 1983.
Olsson, I., and Lund, U., Induction of Differentiation of the Human Histiocytic Lymphoma Cell Line U937 by 1α, 25-Dihydroxycholecalciferol. *Cancer Res.* 43 (12) 5862–5867, 1983.
Eisman, J. A. et al., 1,25-Dihydroxyvitamin-D Receptor in Breast Cancer Cells, *Lancet*, Dec. 22/29: 1335–1336, 1979.
Frampton, R. J. et al., Presence of 1,25-Dihydroxyvitamin $D_3$ Receptors in Established Human Cancer Cell Lines in Culture, *Cancer Res.* 42: 1116–1119, 1982.
Colston, K. et al., 1,25-Dihydroxyvitamin $D_3$ Receptors in Human Epithelial Cancer Cell Lines, *Cancer Res.* 42:856–859, 1982.
Sher, E. et al., Whole Cell Uptake and Nuclear Localization of 1,25-Dihydroxycholecalciferol by Breast Cancer Cells (T47d) in Culture, *Biochem J.* 200: 315–320, 1981.
Frampton, R. J. et al., Inhibition of Human Cancer Cell Growth by 1,25-dihydroxyvitamin $D_3$ Metabolites, *Cancer Res.* 43:4443–4447, 1983.
Shiina, Y. et al., Biological Activity of 24,24-difluoro-1α,25-dihydroxyvitamin $D_3$ and 1α, 25-dihydroxyvitamin $D_3$-26,23-lactone in Inducing Differentiation of Human Myeloid Leukemia Cells, *Arch. Biochem. Biophys.* 220: 90–94, 1983.
Abe, E. et al., Differentiation of Mouse Myeloid Leukemia Cells Induced by 1α,25-dihydroxyvitamin $D_3$, *Proc. Natl. Acad. Sci. USA* 78: 4990–4994, 1981.
McCarthy, D., 1α,25-dihydroxyvitamin $D_3$ Causes Granulocytes from Patients with Chronic Granulocytic Leukemia to Differentiate into Monocytes-macrophages: This Effect is Mediated by a Protein Receptor, *Exp. Hematol.* 11 (Suppl. 14): 200, 1983.
Honma, Y. et al., 1α,25-dihydroxyvitamin $D_3$ and 1α-hydroxy Vitamin $D_3$ Prolong Survival Time of Mice Inoculated with Myeloid *Proc. Natl. Acad. Sci. USA* 80: 201–204, 1983 Leukemia Cells.
Sato, T. et al., Antitumor Effect of 1α-hydroxyvitamin $D_3$, *Tohoku J. Exp. Med.* 138: 445–446, 1982.
McCarthy, D. M., et al., A Role for 1,25-dihydroxyvitamin $D_3$ in Control of Bone Marrow-collagen Deposition? *Lancet*, Jan. 14: 78–80, 1984.
Koeffler et al, "Cancer Research"(1984) vol. 44, pp. 5624–5628.

*Primary Examiner*—Elbert L. Roberts
*Attorney, Agent, or Firm*—Jon S. Saxe; Bernard S. Leon; Matthew Boxer

[57] ABSTRACT

The syntheses of 25,26-dehydro-1α,23S-dihydroxycholecalciferol, 25,26-dehydro-1α,23R-dihydroxycholecalciferol, and the epimeric mixture thereof which are useful as differentiation inducing agents and antiproliferation agents are described, 25,26-dehydro-1α,23S-dihydroxycholecalciferol 25,26-dehydro-1α,23R-dihydroxycholecalciferol and the epimeric mixture thereof are useful for treating tumors and leukemia, and osteoporosis.

6 Claims, No Drawings

25,26-DEHYDRO-1α,23(S,R)-DIHYDROXY-CHOLECALCIFEROL AND ITS EPIMERS

BRIEF SUMMARY OF THE INVENTION

The invention relates to 25,26-dehydro-1α,23S-dihydroxycholecalciferol. its 23R-epimer and the epimeric mixture thereof the formula:

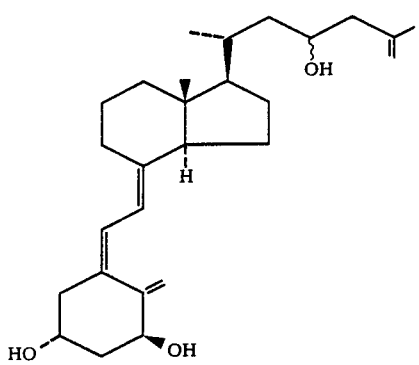

Further aspects of the invention relate to the processes and intermediates utilized to prepare the compounds of formula I and pharmaceutical preparations containing the compounds of formula I.

The compounds of formula I are specific inducers of cell differentiation and inhibitors of cell proliferation. Thus the compounds of formula I are useful in the treatment of proliferative disease states, for example, tumors such as leukemia. The compounds of formula I are also useful in the treatment of osteoporosis.

DETAILED DESCRIPTION OF THE INVENTION

The term "alkanol" refers to a compound derived by protonation of the oxygen atom of an alkoxy group. Examples of alkanols are methanol, ethanol, 2-propanol, 2-methyl-2-propanol and the like. "Lower alkyl" refers to an alkyl of 1 to 8 carbon atoms. The term "alkali metal" referes to lithium, sodium and potassium.

In the formulae presented herein, the various substituents are illustrated as joined to the steroid nucleus by one of these notations: a solid line (——) indicating a substituent which is above the plane of the molecule a dotted line (----) indicating a substituent which is below the plane of the molecule, or a wavy line (∼∼∼) indicating a substituent which may be above or below the plane of molecule, or else indicating the epimeric mixture thereof. Since the starting materials are derived from a naturally occurring steroid, the products exist in the single absolute configuration herein. As described below, one may begin the synthesis of the invention, with either [1R-[1 alpha (R*,S*), 3a beta, 4 beta, 7a alpha]]-octahydro-1-(3-hydroxy-1,5-dimethyl-5-hexenyl)-7a-methyl-1H-inden-4-ol, trimethylsilyl ether or [1R-[1 alpha (R*, R*)-3a beta, 4 beta, 7a alpha]]-octahydro-1-(3-hydroxy-1,5-dimethyl-5-hexenyl)-7a-methyl-1-H-inden-4-ol, trimethylsilyl ether or with the epimeric mixture thereof in order to produce the corresponding 25,26-dehydro-1α,23S-dihydroxycholecalciferol, the 23R-epimer or the epimeric mixture thereof. The epimeric mixture of 25,26-dehydro-1α,23-dihydroxycholecalciferol may be designated 25,26-dehydro-1α,23(S,R)-dihydroxycholecalciferol.

The nomenclature adopted to define absolute configuration of substituents bound to carbon atom 23 of the steroid nucleus is described in the Journal of Organic Chemistry, 34, 2849 (1970) under the title "IUPAC Tentative Rules for the Nomenclature of Organic Chemistry. Section E. Fundamental Stereochemistry."

25,26-dehydro-1α,23S-dihydroxycholecalciferol, its 23R-epimer, or the epimeric mixture thereof are conveniently prepared by synthesis from a trimethylsilyl ether intermediate of the structure:

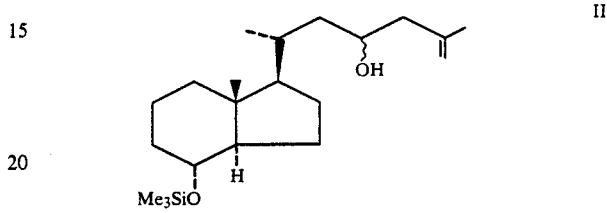

A compound of formula II is converted to a compound of the formula:

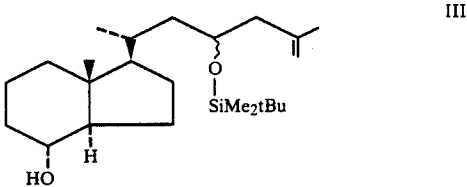

by reaction with a t-butyldimethylsilyl halide, such as t-butyldimethylsilyl chloride, and an organic base such as imidazole. The reaction is conveniently carried out in an inert atmosphere, such as nitrogen or preferably argon and in a suitable aprotic organic solvent or solvent mixture such as cylic ether or an alkylated formamide or preferably mixtures thereof. A preferred solvent is a mixture of dimethylformamide and tetrahydrofuran, in about 5:3 (v/v) mixture.

The temperature of the reaction is about room temperature.

Then known, chromatographic procedures are used to obtain the reaction product. Thus in a preferred embodiment, the residue of the reaction mixture is treated with a cationic exchange resin, such as a styrene type sulfonic acid. This is followed by a silica gel chromatography step which provides the compound of formula III.

In the treatment with a cationic exchange resin, a mixture of a cyclic ether and a lower alkanol is used. A preferred mixture is tetrahydrofuran and methanol in a 1:3 (v/v) mixture.

As seen from the structures of the compounds of formula II and III, the aforesaid reactions remove the trimethylsilyl protecting group from the ring hydroxy moiety.

The next step in the synthesis involves oxidation of the ring hydroxyl group using a chemical oxidation agent. Suitable oxidation agents for this purpose include chromate salts particularly with basic organic amines such as for example pyridinium halochromates, preferably 2,2'-bi-pyridinium chlorochromate. Also added is a salt of a carboxylic acid, preferably sodium acetate. The reaction is carried out under ambient conditions of temperature and pressure using an inert solvent. Suitable inert solvents include the halogenated alkanes, preferably a chloroalkane such as methylene chloride. There is thus obtained a ketone of the formula

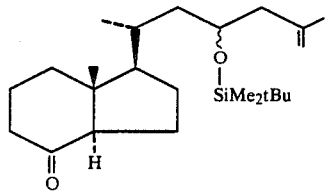

A compound of formula IV is reacted with [3S-(3α,5β,Z)]-2-[2-methylene-3,5-bis[(1,1-dimethylethyl) dimethylsilyloxy]cyclohexylidene] ethyldiphenyl phosphine oxide to yield the corresponding compound of formula V.

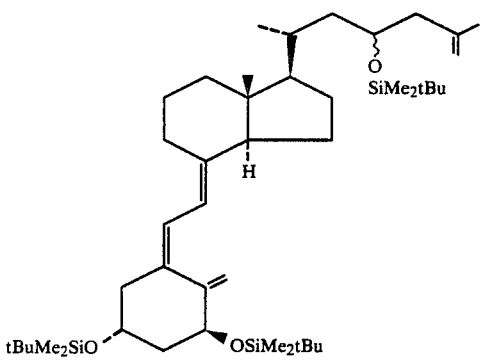

The above reaction is carried out at reduced temperatures e.g. below −50° C., most preferably at about −78° C. using an inert atmosphere such as for example an argon atmosphere. A suitable inert solvent may be employed in carrying out this reaction, for example, a cyclic ether, most preferably tetrahydrofuran. It is desirable to convert the phosphine oxide to a corresponding carbanion to facilitate the desired reaction. This is readily accomplished by initially treating the phosphine oxide with an alkyl lithium such as preferably n-butyl lithium in an inert solvent such as a lower alkane, e.g. hexane at reduced temperatures as above.

In the last step of the synthesis the hydroxyl protecting groups on a compound of formula V are removed to yield a compound of formula I of the invention, that is 25,26-dehydro-1α,23S-dihydroxycholecalciferol, its 23R-epimer or the epimeric mixture thereof.

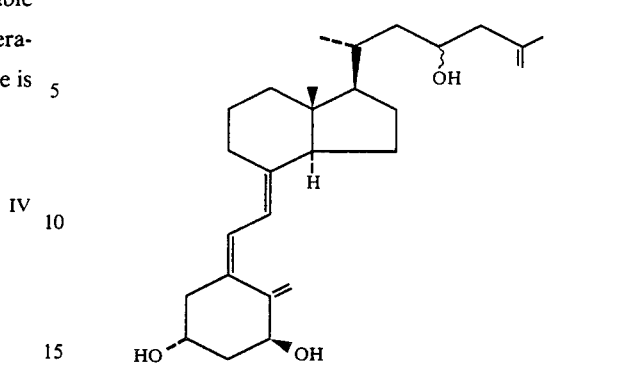

The above reaction is carried out at room temperature by treatment of the compounds of formula V with tetraethylammonium fluoride. The reaction is carried out in the presence of a cyclic ether solvent, preferably in the presence of tetrahydrofuran.

A compound of formula I can be purified by procedures known per se such as, for example, by use of silica gel chromatography.

The starting materials of formula II used in the above described synthesis are readily obtainable as described in U.S. patent application Ser. No. 566,103 filed Dec. 27, 1983.

25,26-dehydro-1α,23S-dihydroxycholecalciferol, its 23R-epimer, or the epimeric mixture thereof, are powerful specific inducers of cell differentiation and inhibitors of cell proliferation. Thus, the compounds are useful agents in the treatment of proliferative disease states, for example tumors, such as leukemia. The compounds are also useful in the treatment of osteoporosis. 25,26-dehydro-1α,23S-dihydroxycholecalciferol, its 23R-epimer, or the epimeric mixture thereof, can be administered in dosages that are in the range of about 0.10–3.0 micrograms/per day. Preferable dosage ranges are 0.25–2.0 micrograms per day. It will, however, be understood that the dosages indicated above are only given by way of example and that they in no way limit the scope of the use of this invention. The compounds of the invention can be administered orally, subcutaneously, intra-muscularly, intravenously, intraperitoneally or topically.

The aforesaid compounds can be formulated into compositions such as tablets, capsules, and the like, or elixirs for oral administration, or in sterile solutions or suspensions for parenteral administration for the treatment of the aforementioned disease states. About 0.10–3.0 micrograms, preferably 0.25–2.0 micrograms, is compounded with a pharmaceutically acceptable vehicle, carrier, excipient, binder, preservative, stablizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as calcium phosphate; a disintegrating agent such as corn starch, potato starch, algenic acid, and the like; a lubricant such as magnesium stearate, sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

The anti-proliferative and differentiation-inducing effects of 25,26-dehydro-1α,23S-dihydroxycholecalciferol were demonstrated in the procedures described just below. These effects indicate that this compound is useful in the treatment of tumors, and leukemia.

GENERAL EXPERIMENTAL DESCRIPTION

Cultures of HL-60 cells were established in the absence (control) or presence of various concentrations of 25,26-dehydro-1α,23S-dihydroxycholecalciferol. After a 4-day incubation period, the cultures were evaluated for proliferation of tumor cells, tumor cell viability, and cellular differentiation. Proliferation was assessed by directly enumerating the increased number of tumor cells resulting from incubation. Viability was determined by dye exclusion technique to learn whether the test compound was lethal to cultured HL-60 cells. Cellular differentiation was evaluated by determining the number of cells which had acquired the enzymes necessary to support a respiratory burst and the functional ability to phagocytose (bind/internalize) particulate material from their environment; both activities being characteristic of mature macrophages and granulocytes.

METHODS

Tissue culture medium used in these experiments was RPMI-1640 supplemented prior to use to 10% v/v with fetal bovine serum (heat inactivated at 56° for 30 minutes), to 130 units per ml with penicillin and 130 μg per ml with streptomycin, and to an additional 1.6 millimolar with L-glutamine.

Test compounds were dissolved in sufficient ethanol to yield stock solutions of $1 \times 10^{-2}$ molar. Reduced lighting was employed when working with compounds and stock solutions were stored in the dark at $-20°$ in an argon atmosphere. Compounds were diluted with tissue culture medium and added to flasks containing HL-60 cells to achieve the final concentrations described in each experiment.

The promyelocytic (HL-60) tumor cell line was derived from a patient with acute promyelocytic leukemia. HL-60 cells were maintained in liquid culture by serial weekly passage in tissue culture medium. In any experiment, three replicate flasks were incubated without compound (control) or in the presence of varying concentrations of compound. After 4 days of incubation at 37° in a humidified atmosphere of 5% $CO_2$ in air, cultures were evaluated for tumor cell proliferation, viability and differentiation.

Quantitation of proliferation was done by enumerating the number of HL-60 cells in each individual flask (3 flasks per experimental point) using a model ZBI Coulter Counter. Results are shown as the number of cells per ml of tissue culture medium expressed as the means ± standard deviation and as percent reduction of cell number calculated according to the formula:

$$\left(1 - \frac{\text{mean number of cells in experimental cultures}}{\text{mean number of cells in control cultures}}\right) \times 100$$

Experimental cultures with the same or slightly greater cell numbers than control cultures are reported as zero percent reduction.

Viability of tumor cells was determined by the method of trypan blue dye exclusion. Cells in tissue culture medium were added to a four-fold larger volume of 0.4% trypan blue in saline. Cells were scored as viable upon microscopic examination if they excluded dye and as dead if they were stained blue. The viability of cells from all experimental cultures was never less than that from control cultures indicating that the compound tested was not toxic to HL-60 cells in the concentrations employed.

Quantitation of differentiated cells was done by the biochemical method of nitroblue tetrazolium (NBT) reduction. Sufficient cells was pooled from replicate cultures, centrifuged at $220 \times g$, washed once with serum-free tissue culture medium, and resuspended to $1 \times 10^6$ cells per ml in $Ca^{++}$-$Mg^{++}$-deficient phosphate buffered saline (prepared by supplementing $Ca^{++}$-$Mg^{++}$-free phosphate buffered saline (PBS) to 10% v/v with heat-inactivated fetal bovine serum). Nitroblue tetrazolium was dissolved at 1 mg per ml in $Ca^{++}$-$Mg^{++}$-deficient PBS with gentle heating and mixing. Tetradecanoyl phorbol acetate (TPA) was dissolved at 1 mg use, a working solution of TPA was prepared by diluting the stock concentration 100-fold with $Ca^{++}$-$Mg^{++}$-deficient PBS. The test was done in $12 \times 75$ mm tubes by adding 0.5 ml $Ca^{++}$-$Mg^{++}$-deficient PBS, 1.0 l of HL-60 cells, 0.5 ml of NBT solution, and 0.02 ml of the working TPA solution. After mixing, the tubes were incubated in a 37° water bath for 25 min then transferred to ice. Undifferentiated and differentiated cells present in any sample were determined microscopically by surveying 200–400 cells per sample. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results were expressed as the percentage of differentiated cells present in any sample as calculated according to the formula:

$$100 \times \frac{\text{number of formazan positive cells}}{\text{total number of cells counted}} = \% \text{ ``+''}.$$

Quantitation of differentiated HL-60 cells on a functinal basis was done by enumerating the number of cells in any sample which had acquired the ability to phagocytose (bind/internalize) particulate material from their environment, a characteristic of mature macrophages and granulocytes. Sufficient cells were pooled from replicate cultures, centrifuged at $200 \times g$, washed once with serum-free tissue culture medium, and resuspended to $1 \times 10^6$ cells per ml in serum-free tissue culture medium. To a 1.0 ml sample in $12 \times 75$ mm tubes was added 0.1 ml of a 1:10 dilution from stock of fluorescent microspheres. Yeast or latex beads can also be used in place of fluorescent microspheres at this stage. Cells and particle were mixed, incubated for 15 minutes in a 37° water bath, collected in a transfer pipet, and overlayed onto a 5 ml cushion of fetal bovine serum in a 15 ml conical culture tube. After centrifugation at $150 \times g$ for 8 minutes, the excess particulate (upper layer) was discarded as was the remainder of the serum cushion leaving only a cell pellet and cell-associated particulate. The resultant pellets were resuspended in 1.0 ml of tissue culture medium containing 10% fetal bovine serum, transferred to a hemacytometer, and evaluated microscopically using both ultraviolet and visible light sources. Undifferentiated and differentiated cells present in any sample were determined microscopically by surveying 200–400 cells per sample. Non-fluorescent cells, identified only by visible light, were judged to be undifferentiated. Generally, differentiated cells were intensely fluorescent clearly indicating extensive phagocytosis of particulate material. Results are expressed as the percentage of differentiated cells present in any sample as calculated according to the formula:

$$100 \times \frac{\text{number of phagocytic cells}}{\text{total number of cells counted}}.$$

RESULTS

Anti-proliferative and differentiation-inducing effects of 25,26-dehydro-1α,23S-dihydroxycholecalciferol In the experiment, HL-60 cells were cultured with 1, 3, 10, 30 and $100 \times 10^{-9}$ molar concentrations of 25,26-dehydro-1α,23S-dihydroxycholecalciferol for 4 days. Cellular proliferation was evaluated by direct cell enumeration while induction of cellular differentiation was assessed by NBT reduction. As shown in TABLE I, ethanol, used as vehicle, had no effect on cellular proliferation or differentiation or phagocytosis (compare vehicle control cultures to medium control cultures) and therefore did not contribute to the effects produced by the compound of the invention. Cellular proliferation was inhibited in a dose-dependent fashion by 25,26-dehydro-1α,23S-dihydroxycholecalciferol and a plateau in the anti-proliferative effect was suggested between the doses of 10 and $100 \times 10^{-9}$ molar (see, TABLE I). Data from the NBT reduction test similarly reveal the differentiation inducing effect of the experimental compound to be dose-related. Because the proportion of cells capable of enzymatically reducing NBT and performing the function of phagocytosis increased with the concentration of compound, it is concluded that 25,26-dehydro-1α,23S-dihydroxycholecalciferol induced cellular differentiation.

These data indicate that the compound evaluated restrained the proliferation of human promyelocytic tumor cells in vitro even though the compound was not directly toxic to the cells. Furthermore, cells cultured in the presence of low doses of compound (3 to $100 \times 10^{-9}$ molar) were induced to differentiate toward a more mature cell type as evidenced by the acquisition of enzyme activity and cellular function. Accordingly, the compounds of formula I represent a unique approach to the management of clinical diseases which owe to aberrant cellular proliferation and/or differentiation. For example, the compounds of formula I are useful in the management of neoplastic disease which owes in part to a perturbation of the normal processes of cellular differentiation.

TABLE I

ANTI-PROLIFERATIVE AND DIFFERENTIATION-INDUCING EFFECTS OF 1α,23S—(OH)$_2$ $\Delta^{25}$-D$_3$ ON HL-60 CELLS, IN VITRO[d]

| Compound and[a] Concentration ($\times 10^{-9}$ molar) | Proliferation[b] | | Differentiation[c] | | | |
|---|---|---|---|---|---|---|
| | HL-60 cells per ml $\times 10^{-4}$ | % reduction of cell number | NBT reduction | | phagocytosis | |
| | | | formazan "+" cells total cells counted | % "+" | phagocytic cells total cells counted | % "+" |
| None (medium control) | 79.1 ± 1.4 | — | 3/437 | <1 | 3/325 | <1 |
| Vehicle (0.01% ethanol) | 75.9 ± 2.0 | 0 | 3/431 | <1 | 2/364 | <1 |
| 1α,23S—(OH)$_2$ $\Delta^{25}$-D$_3$ 1 | 74.7 ± 2.2 | 2 | 2/419 | <1 | 3/335 | 1 |
| 1α,23S—(OH)$_2$ $\Delta^{25}$-D$_3$ 3 | 75.2 ± 0.7 | 1 | 10/436 | 2 | 6/367 | 2 |
| 1α,23S—(OH)$_2$ $\Delta^{25}$-D$_3$ 10 | 58.0 ± 2.0 | 24 | 100/434 | 23 | 60/354 | 17 |
| 1α,23S—(OH)$_2$ $\Delta^{25}$-D$_3$ 30 | 35.7 ± 1.2 | 53 | 247/428 | 58 | 201/417 | 48 |
| 1α,23S—(OH)$_2$ $\Delta^{25}$-D$_3$ 100 | 23.7 ± 0.5 | 69 | 361/400 | 90 | 315/383 | 82 |

[a]The final vehicle concentration in all experimental cultures was 0.01%, v/v, ethanol.
[b]Triplicate cultures were established with $2 \times 10^4$ cells per ml and incubated for 4 days. Cell density was determined for each culture vessel and results are expressed as mean cell number ± standard deviation ($\times 10^{-4}$). The viability of cells from all cultures was ≧96%.
[c]Differentiated cells were determined by the methods of enzymatic reduction of NBT to formazan and phagocytosis and were enumerated microscopically.
[d]1α,23S—(OH)$_2$ $\Delta^{25}$-D$_3$ is 25,26-Dehydro-1α,23S—dihydroxycholecalciferol.

EXAMPLE 1

Preparation of [1R-[alpha(R*,S*)3abeta,4abeta,7aalpha]]-octahydro-1-[3-((1,1-dimethylethyl)-dimethylsilyloxy)-1,5-dimethyl-5-hexenyl)-7a-methyl-1H-inden-4-ol A solution of 0.352 g of [1R-[1alpha(R*,S*),3abeta,4beta,7aalpha]]-octahydro-1-(3-hydroxy-1,5-dimethyl-5-hexenyl)-7a-methyl-1H-inden-4-ol, trimethylsilyl ether, 0.31 g. of t-butyldimethylsilyl chloride and 0.31 g. of imidazole in 5 ml of dry dimethylformamide and 3 ml of dry tetrahydrofuran was stirred under an atmosphere of argon, at room temperature overnight, after which a few pieces of ice were added. After stirring 30 minutes the mixture was taken up in 200 ml of hexane/ether (5:1) and washed 10×8 ml of H$_2$O, 1×10 ml of brine and dried over Na$_2$SO$_4$. The mixture was filtered and solvents removed in vacuo to give 0.576 g of material. This was stirred for 1 hour with 0.1 g of a cation exchange resin AG50W-X4, Bio-Rad Laboratories in 5 ml of tetrahydrofuran and 15 ml of methanol. The mixture was filtered and solvents removed in vacuo. The residue was purified by chromatography on silica gel eluting with hexane/ethyl acetate (10:1) to give 0.316 g of [1R-[1alpha(R*,S*)-3abeta,4abeta,7aalpha]]-octahydro-1-(3-((1,1-dimethylethyl)-dimethylsiloxy)-1,5-dimethyl-5-hexenyl),-7a-methyl-1H-inden-4-ol which was used directly in the next step.

EXAMPLE 2

Preparation of [1R[1alpha(R*,S*)-3abeta,7aalpha]]-octahydro-1-(3-((1,1-dimethylethyl)-dimethylsiloxy)-1,5-dimethyl-5-hexenyl-7a-methyl-1H-inden-4-one A solution of 0.24 g of [1R-[1alpha(R*,S*)-3abeta,-4abeta,7aalpha]]-octahydro-1-[3-((1,1-dimethylethyl)-dimethylsilyloxy)-1,5-dimethyl-5-hexenyl)-7a-methyl-1H-inden-4-ol in 15 ml of dry methylene chloride was treated with 0.35 g of anhydrous sodium acetate and 0.71 g of 2,2'-bipyridinium chlorochromate and the mixture stirred at room temperature for 3 hours. After this time an additional 0.355 g of 2,2'-bipyridinium chlorochromate was added. The mixture was stirred 2 hours then 1 ml of isopropanol was added, mixture stirred for 20 minutes then diluted with water and extracted with ether/ethyl acetate 1:1. The combined organic phases were washed with water, then brine, dried over anhydrous sodium sulfate, filtered and the solvents removed in vacuo. The residue was purified by silica gel chromatography eluting with hexane/ethyl acetate (4:1) to give 0.238 g of pure [1R-[1alpha(R*,S*)-3abeta,7aalpha]]octahydro-1-[3-((1,1-dimethylethyl)-dimethylsilyloxy)-1,5-dimethyl-5-hexenyl)-7a-methyl-1H-inden-4-one.

EXAMPLE 3

Preparation of (1alpha,3beta,5Z,7E,23S)-9,10-secocholesta-5,7,10(19),25-tetraene-1,3,23-triol A solution of 0.265 g of [3S-(3alpha,5beta,Z)]-2-[2-methylene-3,5-bis-[(1,1-dimethylethyl)-dimethylsiloxyl]cyclohexylidene]ethyldiphenyl phosphine oxide in 6 ml of anhydrous tetrahydrofuran was cooled at −78° C. and treated dropwise with 0.276 ml of a 1.6M solution of n-butyllithium in hexane. After stirring 5 minutes at −78° C., the deep red solution was treated dropwise with 0.1 g of [1R[1alpha(R*,S*)-3abeta,7aalpha]]-octahydro-1-(3-((1,1-dimethylethyl)-dimethylsiloxy)-1,5-dimethyl-5-hexenyl)-7a-methyl-1H-inden-4-one dissolved in 2.5 ml of anhydrous tetrahydrofuran. The mixture was stirred 1.5 hours then quenched by addition of 3 ml of 1:1 mixture of 1N sodium bicarbonate and 1N sodium potassium t artrate, allowed to warm to room temperature then diluted with water and extracted with ethyl acetate. The combined organic extracts were washed with water, then brine, dried over anhydrous sodium sulfate, filtered and solvents removed in vacuo. The residue was purified by chromatography on silica gel eluting with hexane/ethyl acetate (20:1) to give 0.130 g of the trisilyl ether. This was dissolved in 6 ml of tetrahydrofuran and treated with 1.3 ml of 1M tetrabutylammonium fluoride in tetrahydrofuran and stirred at room temperature for 20 hours. Then 0.5 ml of 1M tetrabutylammonium fluoride in tetrahydrofuran was added and stirring continued for 4 hours. The mixture was diluted with water and extracted with ethyl acetate. The combined organic extracts were washed with water, then brine, dried over anhydrous sodium sulfate, filtered and volatiles removed in vacuo. The residue was purified by chromatography on silica gel eluting with hexane/ethyl acetate (1:4) to give 0.079 g of pure (1alpha,3beta,5Z,7E,23S)-9,10-secocholesta-5,7,10(19),25-tetraene-1,3,23-triol as a white amorphous powder $[\alpha]^{25}D$ +37.97° (c 0.2, EtOH).

EXAMPLE 4

Preparation of [1R-[1alpha(R*,R*)3abeta,4beta,7aalpha]]-octahydro-1-((3-(1,1-dimethylethyl)-dimethylsilyloxy)-1,5-dimethyl-5-hexenyl)-7a-methyl-1H-inden-4-ol Following the procedure of Example 1, [1R-[1alpha(R*,R*)-3abeta,4beta,7aalpha]]-octahydro-1-(3-hydroxy-1,5-dimethyl-5-hexenyl)-7a-methyl-1-H-inden-4-ol, trimethylsilyl ether is converted to [1R-[1alpha(R*,R*)-3abeta,4beta,7aalpha]]-octahydro-1-(3-((1,1-dimethylethyl)-dimethylsiloxy)-1,5-dimethyl-5-hexenyl)-7a-methyl-1H-inden-4-ol.

EXAMPLE 5

Preparation of [1R[1alpha(R*,R*)-3abeta,7aalpha]]-octahydro-1-(3-((1,1-dimethylethyl)-dimethylsiloxy)-1,5-dimethyl-5-hexenyl)-7a-methyl-1H-inden-4-one Following the procedure of Example 2, 1R-[1alpha(R*,R*)-3abeta,4beta,-7aalpha]]-octahydro-1-(3-((1,1-dimethylethyl)-dimethylsilyloxy)-1,5-dimethyl-5-hexenyl)-7a-methyl-1H-inden-4-ol is converted to [1R[1alpha-(R*,R*)-3abeta,7aalpha]]-octahydro-1-(3-((1,1-dimethylethyl)-dimethylsilyloxy)-1,5-dimethyl-5-hexenyl)-7a-methyl-1H-inden-4one.

EXAMPLE 6

Preparation of (1alpha,3beta,5Z,7E,23R)-9,10-secocholesta-5,7,10(19),25-tetraene-1,3,23-triol Following the procedure of Example 3, [1R[1alpha(R*,R*)-3abeta,-7aalpha]]-octahydro-1-(3-((1,1-dimethylethyl)-dimethylsilyloxy)-1,5-dimethyl-5-hexenyl)-7a-methyl-1H-inden-4-one is converted to (1alpha,-3beta,5Z,7E,23R)-9,10-secocholesta-5,7,10(19),25-tetraene-1,3,23-triol.

In any of the examples of formulations given below, 25,26-dehydro-1α,23R-dihydroxycholecalciferol or the epimeric mixture, 25,26-dehydro-1α,23(S,R)-dihydroxycholecalciferol may be used in place of the 23S-epimer. For instance, in Example 7, first column on the left, 0.00010 mg of the mixture 25,26-dehydro-1α,23(S,R)-dihydroxycholecalciferol may be used in place of 0.00010 mg of the 23S-epimer.

| Item | Ingredients | mg/capsule | | |
|---|---|---|---|---|
| 1. | 25,26-dehydro-1α,23S—dihydroxy-cholecalciferol | 0.00010 | 0.00025 | 0.00050 |
| 2. | polyethylene glycol 400 (PEG 400) | 200.00 | 200.00 | 200.00 |
| 3. | butylated hydroxy anisole (BHA) | 0.100 | 0.100 | 0.100 |
| 4. | ascorbyl palmitate | 1.00 | 1.00 | 1.00 |

PROCEDURE

Dissolve items 1, 3 and 4 in item 2, under a blanket of nitrogen and encapsulate.

EXAMPLE 8

| Item | Ingredients | mg/capsule | |
|---|---|---|---|
| 1. | 25,26-dehydro-1α,23S—dihydroxycholecalciferol | 0.10 ml | 0.50 ml |
| 2. | 95% ethanol - 5% water | 2.00 ml | 3.00 ml |

PROCEDURE

Dissolve item 1 in item 2 under a blanket of nitrogen and inject intramuscularly.

We claim:

1. A compound 25,26-dehydro-1α,23S-dihydroxy-cholecalciferol, the 23R-epimer, or the epimeric mixture thereof.

2. The compound in accordance with claim 1, 25,26-dehydro-1α,23S, dihydroxycholecalciferol.

3. A method for treating tumors which comprises administering a therapeutically effective amount of 25,26-dehydro-1α,23S-dihydroxycholecalciferol, the 23R-epimer or the epimeric mixture thereof.

4. A method in accordance with claim 3, wherein the compound is 25,26-dehydro-1α,23S-dihydroxycholecalciferol.

5. A pharmaceutical composition comprising an effective amount of a compound 25,26-dehydro-1α,23S-dihydroxycholecalciferol, the 23R-epimer or the epimeric mixture thereof and an inert pharmaceutical carrier material.

6. A composition in accordance with claim 5 wherein the compound is 25,26-dehydro-1α,23S-dihydroxycholecalciferol.

* * * * *